United States Patent
Lin et al.

(10) Patent No.: US 12,258,562 B2
(45) Date of Patent: Mar. 25, 2025

(54) ARTIFICIAL NON-CODING RNA MODULE FOR ENHANCING NITROGEN FIXATION ABILITY OF MICROORGANISMS

(71) Applicant: BEIJING GREENBIO-TECH CO., LTD, Beijing (CN)

(72) Inventors: Min Lin, Beijing (CN); Yuhua Zhan, Beijing (CN); Yongliang Yan, Beijing (CN); Xiubin Ke, Beijing (CN)

(73) Assignee: BEIJING GREENBIO-TECH CO., LTD, Beijing (CN)

( * ) Notice: Subject to any disclaimer, the term of this patent is extended or adjusted under 35 U.S.C. 154(b) by 176 days.

(21) Appl. No.: 18/008,674

(22) PCT Filed: Jul. 6, 2020

(86) PCT No.: PCT/CN2020/100412
§ 371 (c)(1),
(2) Date: Dec. 7, 2022

(87) PCT Pub. No.: WO2021/253521
PCT Pub. Date: Dec. 23, 2021

(65) Prior Publication Data
US 2023/0227827 A1 Jul. 20, 2023

(30) Foreign Application Priority Data
Jun. 16, 2020 (CN) .......................... 202010545585.0

(51) Int. Cl.
*C12N 15/31* (2006.01)
*C12N 9/02* (2006.01)
*C12N 15/113* (2010.01)
*C12N 15/74* (2006.01)

(52) U.S. Cl.
CPC .......... *C12N 15/113* (2013.01); *C12N 9/0004* (2013.01); *C12N 15/74* (2013.01); *C12Y 118/06001* (2013.01); *C12N 2510/02* (2013.01)

(58) Field of Classification Search
None
See application file for complete search history.

(56) References Cited

FOREIGN PATENT DOCUMENTS

| CN | 103451130 A | 12/2013 |
| CN | 103525830 A | 1/2014 |
| CN | 104862315 A | 8/2015 |
| CN | 104046635 | * 5/2017 |

OTHER PUBLICATIONS

Zhan et al, The novel regulatory ncRNA, NfiS, optimizes nitrogen fixation via base pairing with the nitrogenase gene nifK mRNA in Pseudomonas stutzeri A1501, PNAS, 2016, pp. E4348-4356.*
Dos Santos et al. Distribution of nitrogen fixation and nitrogenase-like sequences amongst microbial genomes, BMC Genomics 2012, pp. 1-12.*
Bennett EM, Murray JW, Isalan M. Engineering Nitrogenases for Synthetic Nitrogen Fixation: From Pathway Engineering to to Directed Evolution. BioDesign Res., 2023, pp. 1-12.*
Yuhua Zhan, et al., NfiR, a New Regulatory Noncoding RNA (ncRNA), Is Required in Concert with the NfiS ncRNA for Optimal Expression of Nitrogenase Genes in Pseudomonas stutzeri A1501, Applied and Environmental Microbiology, 2019, pp. 1-18, vol. 85, Issue 14, e00762-19.
Hongyang Zhang, et al., The Pseudomonas stutzeri-specific regulatory ncRNA, NfiS, targets the katB mRNA encoding a catalase essential for optimal oxidative resistance and nitrogenase activity, Journal of Bacteriology, 2019, pp. 1-37.
Yan Yongliang, et al., Advancement in artificial design of biological nitrogen fixation system, Biotechnology & Business, 2019, pp. 34-40, abstract only in English.

* cited by examiner

*Primary Examiner* — Maria Marvich
(74) *Attorney, Agent, or Firm* — Bayramoglu Law Offices LLC

(57) ABSTRACT

An artificial non-coding RNA (ncRNA) module constructed by a synthetic biology technique and the use of the artificial ncRNA module in the construction of an artificial nitrogen fixation system are disclosed. The RNA module can enhance the post-transcriptional stability of nifHDK mRNA by interacting with a nitrogenase coding gene nifHDK mRNA, thereby improving the nitrogen fixation ability of a chassis microorganism. A fusion expression vector carrying the artificial RNA module is constructed and transformed into different chassis nitrogen-fixing microorganisms. It is confirmed through experiments that, under nitrogen fixation conditions, the artificial RNA module of the present disclosure can significantly improve the nitrogenase activity of a recombinant engineering bacterial strain.

8 Claims, 3 Drawing Sheets
Specification includes a Sequence Listing.

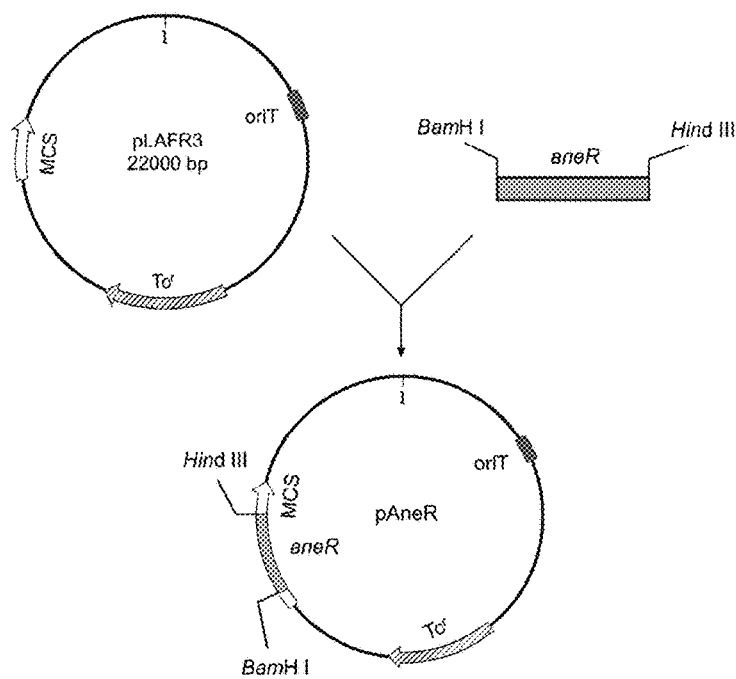
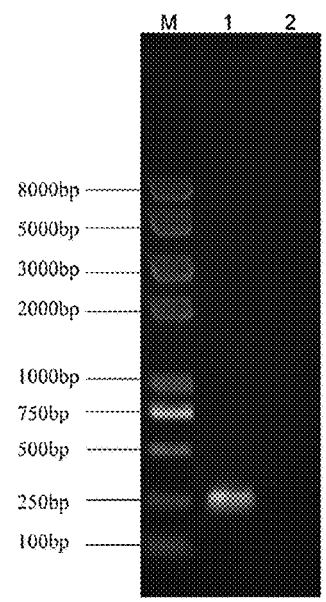
FIG. 1A
FIG. 1B
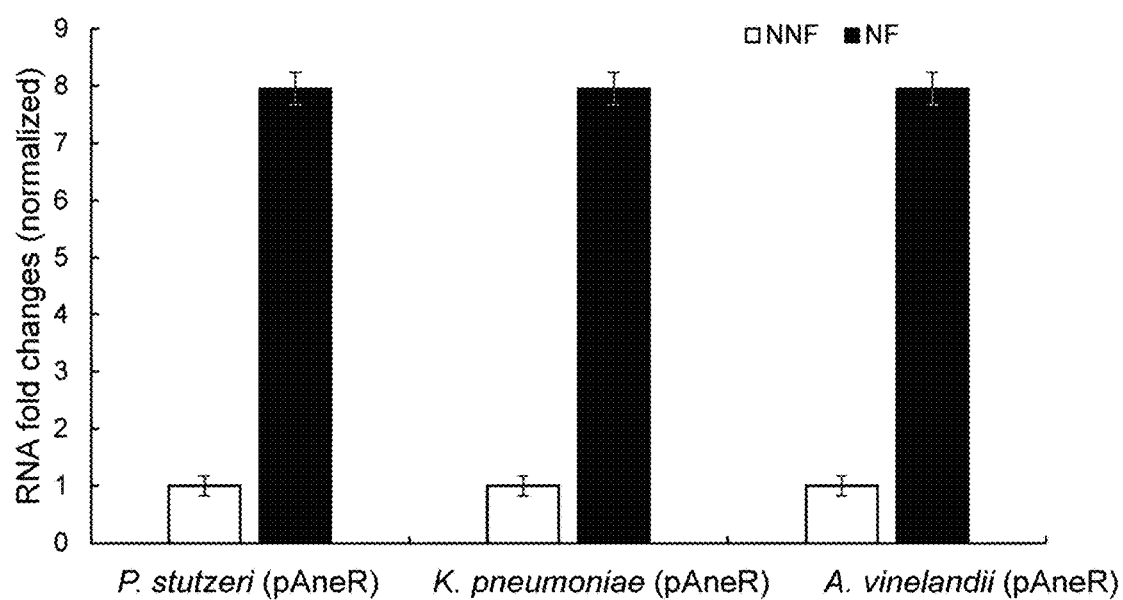
FIG. 2

SEQUENCE LISTING

<160> NUMBER OF SEQ ID NOS: 3

<210> SEQ ID NO 1
<211> LENGTH: 505
<212> TYPE: DNA
<213> ORGANISM: Artificial Sequence
<220> FEATURE:
<223> OTHER INFORMATION: The sequence is synthetized.

<400> SEQUENCE: 1

| | | | | | |
|---|---|---|---|---|---|
| gggagcgtgc | atgcaacccc | ttgatatatg | gggctttgaa | tgcggcgata | gttgccgttc | 60 |
| aggtgttttc | gaaagtatcg | aacgcgacaa | ttgtcatgtt | cgcaacagtt | gccgaaagtg | 120 |
| tggaaaaccg | gcgcttggcc | cggccgatct | ttttgtcgcc | attgcaacag | tcaggcctgt | 180 |
| cggttgttaa | ctatcgaacc | gccgaaggat | gttgctagta | attaaattat | tctaattaaa | 240 |
| acaagtgctt | agattatttt | agaaacgctg | gcacaaaggc | tgctattgcc | ctgttgcgca | 300 |
| ggcttgttcg | tgcctatagc | ccacgtcaag | tggtaacgaa | acctgaggaa | cttaattatg | 360 |
| gcggcggtct | tcggcacagc | agcagcaagg | cggcatcccg | ccgtgcgcgc | catgggtgcc | 420 |
| cgaatcatgc | tcgccatgga | ctgccggcgg | gtgcagcgcg | gcggtcttgc | ctgctgcacc | 480 |
| tctgacccct | caacgtggagc | ggcag | | | | 505 |

<210> SEQ ID NO 2
<211> LENGTH: 145
<212> TYPE: DNA
<213> ORGANISM: Artificial Sequence
<220> FEATURE:
<223> OTHER INFORMATION: The sequence is synthetized.

<400> SEQUENCE: 2

| | | | | | |
|---|---|---|---|---|---|
| gcggcggtct | tcggcacagc | agcagcaagg | cggcatcccg | ccgtgcgcgc | catgggtgcc | 60 |
| cgaatcatgc | tcgccatgga | ctgccggcgg | gtgcagcgcg | gcggtcttgc | ctgctgcacc | 120 |
| tctgacccct | caacgtggagc | ggcag | | | | 145 |

<210> SEQ ID NO 3
<211> LENGTH: 360
<212> TYPE: DNA
<213> ORGANISM: Artificial Sequence
<220> FEATURE:
<223> OTHER INFORMATION: The sequence is synthetized.

<400> SEQUENCE: 3

| | | | | | |
|---|---|---|---|---|---|
| gggagcgtgc | atgcaacccc | ttgatatatg | gggctttgaa | tgcggcgata | gttgccgttc | 60 |
| aggtgttttc | gaaagtatcg | aacgcgacaa | ttgtcatgtt | cgcaacagtt | gccgaaagtg | 120 |
| tggaaaaccg | gcgcttggcc | cggccgatct | ttttgtcgcc | attgcaacag | tcaggcctgt | 180 |
| cggttgttaa | ctatcgaacc | gccgaaggat | gttgctagta | attaaattat | tctaattaaa | 240 |
| acaagtgctt | agattatttt | agaaacgctg | gcacaaaggc | tgctattgcc | ctgttgcgca | 300 |
| ggcttgttcg | tgcctatagc | ccacgtcaag | tggtaacgaa | acctgaggaa | cttaattatg | 360 |

ARTIFICIAL NON-CODING RNA MODULE FOR ENHANCING NITROGEN FIXATION ABILITY OF MICROORGANISMS

CROSS REFERENCE TO THE RELATED APPLICATIONS

This application is the national phase entry of International Application No. PCT/CN2020/100412, filed on Jul. 6, 2020, which is based upon and claims priority to Chinese Patent Application No. 202010545585.0, filed on Jun. 16, 2020, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBDGG077-PKG_Sequence_Listing.txt, created on 12/06/2022, and is 2,131 bytes in size.

TECHNICAL FIELD

The present disclosure relates to the field of biotechnology and, in particular, to an artificial non-coding RNA (ncRNA) module for enhancing a nitrogen fixation ability of a microorganism, and the use thereof in nitrogen fixation synthetic biology.

BACKGROUND

Biological nitrogen fixation is a unique physiological function of nitrogen-fixing microorganisms. The unique physiological function is conducted under a catalytic action of nitrogenase and is greatly affected by intracellular energy supply and environmental stress factors. To adapt to environmental changes, nitrogen-fixing microorganisms have formed a complex regulatory system during evolution, and nitrogen-fixing cells need to express and maintain enough nitrogen-fixing gene (nif) mRNA molecules to ensure high nitrogenase activity.

Natural nitrogen fixation systems are greatly affected by the environment and thus have low nitrogen fixation efficiency, which greatly limits the application of natural nitrogen fixation systems in agricultural production. Therefore, the use of synthetic biology techniques to artificially design a standardized intelligent signal response component and functional module, construct a high-efficiency nitrogen fixation gene circuit, investigate an adaptation mechanism in a microbial chassis, and create a novel artificial nitrogen fixation system is a new strategy and way to improve the biological nitrogen fixation efficiency and realize the wide application in agriculture.

Non-coding RNA (ncRNA) is a very important post-transcriptional regulator. By pairing with mRNA bases, ncRNA inhibits or activates the expression of a target gene at a post-transcriptional level to play an important regulation role in different metabolic regulation processes of bacteria. It has also been found that various ncRNAs may be involved in the expression regulation of nitrogen fixation genes in nitrogen-fixing bacteria, among which ncRNAs NfiR and NfiS participate in the regulation of nitrogenase activity by interacting with nitrogenase genes nifD and nifK mRNA, respectively.

Therefore, because ncRNAs can participate in the regulation of nitrogenase activity, ncRNAs are artificially designed to construct an artificial nitrogen fixation system that is efficient.

SUMMARY

The present disclosure is intended to design and synthesize an artificial ncRNA module for constructing various artificial efficient nitrogen fixation systems.

The present disclosure provides an artificial ncRNA module (Artificial Nitrogenase activity-Enhancing non-coding RNA), which is named AneR and includes the following elements:

(1) an artificial RNA coding sequence including a complementary pairing region with a nitrogenase coding gene nifHDK mRNA, where the artificial RNA coding sequence has a nucleotide sequence shown in SEQ ID NO: 2 and (2) a $\sigma^{54}$-dependent artificial promoter element for initiating the transcription of the artificial RNA coding gene, where the $\sigma^{54}$-dependent artificial promoter element has a nucleotide sequence shown in SEQ ID NO: 3.

The principle of the artificial ncRNA module AneR of the present disclosure to improve the nitrogen fixation ability of a chassis microorganism is as follows: AneR can enhance the post-transcriptional stability of nifHDK mRNA by interacting with a nitrogenase coding gene nifHDK mRNA.

In the present disclosure, an expression vector pAneR carrying the artificial RNA module is constructed, and the expression of the artificial RNA module is controlled by an artificial promoter undergoing inducible expression under nitrogen fixation conditions. The fusion vector is transformed into 3 nitrogen-fixing microbial chassis (*Pseudomonas stutzeri* (*P. stutzeri*), *Klebsiella pneumoniae* (*K. pneumoniae*), and *Azotobacter vinelandii* (*A. vinelandii*)) to obtain 3 recombinant engineering bacterial strains each with a novel artificial nitrogen fixation circuit.

It is confirmed through experiments that, under nitrogen fixation conditions, the artificial RNA module AneR of the present disclosure can significantly improve the nitrogenase activity of various recombinant engineering bacterial strains.

Through the following specific work, the present disclosure constructs the above artificial RNA functional module and verifies its function:

1. Design and Synthesis of the Artificial RNA Module AneR

Based on sequence conservation of the nitrogenase coding gene nifHDK mRNA in the nitrogen-fixing bacteria *P. stutzeri*, *K. pneumoniae*, and *A. vinelandii*, an artificial RNA functional module AneR carrying a complementary pairing region with degeneracy is synthesized by an artificial chemical synthesis method. The expression of AneR is controlled by an artificial promoter that specifically responds to a nitrogen fixation signal, and AneR can cause the inhibited unwinding of a secondary structure through complementary base pairing with the nitrogenase coding gene nifHDK mRNA in the three bacterial strains, thereby resulting in the efficient expression of the nitrogenase gene. AneR has a nucleotide sequence shown in SEQ ID NO: 1.

2. A Fusion Expression Vector Carrying the Artificial RNA Module Aner is Constructed and Transformed Into Three Different Nitrogen-Fixing Microbial Chassis to Obtain Three Recombinant Nitrogen-Fixing Engineering Bacterial Strains

(1) Construction of an AneR-Containing Fusion Expression Vector

The synthetic AneR fragment is subjected to double enzyme digestion with Barn HI and Hind III and inserted into a multiple cloning site (MCS) of a broad-host-range expression vector pFLAα3 to obtain the fusion expression vector pAneR carrying the artificial RNA of the present disclosure (FIGS. 1A and 1B).

(2) Construction of the Three Recombinant Nitrogen-Fixing Engineering Bacterial Strains The expression vector is transformed into the chassis microorganisms *P. stutzeri, K. pneumoniae*, and *A. vinelandii* to obtain the three recombinant engineering bacterial strains *P. stutzeri* (pAneR), *K. pneumoniae* (pAneR), and *A. vinelandii* (pAneR).

3. Analysis of Nitrogen Fixation Abilities of the Recombinant Nitrogen-Fixing Engineering Bacterial Strains

(1) Analysis of a Response of the Artificial RNA Module AneR to a Nitrogen Fixation Stress Signal The expression of the artificial RNA module in the three recombinant bacterial strains under nitrogen fixation conditions is analyzed by the qRT-PCR technology, and analysis results show that a transcription level of AneR in each of the three recombinant bacterial strains under nitrogen fixation conditions is significantly increased by 1.5 times or more compared with that under non-nitrogen fixation conditions (FIG. 2).

(2) Determination of the Nitrogenase Activity in Each of the Recombinant Nitrogen-Fixing Engineering Bacterial Strains The nitrogenase activity of a chassis bacterial strain is compared with that of a recombinant bacterial strain under nitrogen fixation conditions through acetylene reduction, and results show that the nitrogenase activity in each of the recombinant bacterial strains is significantly increased by about 20% compared with that in a corresponding chassis bacterial strain (FIG. 3).

4. Analysis of the Binding Ability of the Artificial RNA Module AneR to the Nitrogenase Coding Gene nifHDK mRNA The microscale thermophoresis (MST) technology is used to analyze the binding between AneR and nifHDK mRNA, and results show that MST fitting curves of the RNA module AneR with nifH/nifD/nifK mRNA are all typical "S" curves, indicating that there is a prominent binding trend between the RNA module AneR and nifH/nifD/nifK mRNA (FIGS. 4A-4C).

5. Analysis of the Artificial RNA Functional Module AneR on the Stability of the Nitrogenase Gene nifHDK mRNA A half-life of nifHDK mRNA in each of A1501 and *P. stutzeri* (pAneR) under nitrogen fixation conditions is analyzed by the qRT-PCR technology, and results show that a half-life of nifHDK mRNA in the recombinant bacteria is significantly extended, where the half-life of nifHDK mRNA in the recombinant bacteria is about 25 min and a half-life of nifHDK mRNA in the wild type (WT) bacteria is about 20 min (FIG. 5).

The present disclosure has the following beneficial effects:

It is confirmed through experiments that, under nitrogen fixation conditions, the artificial RNA module AneR of the present disclosure can significantly improve the nitrogenase activity of various recombinant engineering bacterial strains and significantly enhance the nitrogen fixation ability of a nitrogen-fixing microbial chassis.

The promoter sequence of the present disclosure can be used for the efficient expression of nitrogen fixation genes in different bacteria, and thus, can be used for the construction of various artificial efficient nitrogen-fixing systems.

BRIEF DESCRIPTION OF THE DRAWINGS

FIGS. 1A-1B show the construction of an expression vector carrying an artificial RNA module AneR, where a is a schematic diagram illustrating the construction of the expression vector carrying the artificial RNA module AneR, in which an arrow indicates a gene transcription direction and Barn HI and Hind III indicate insertion sites and b shows the PCR verification of the expression vector pAneR.

FIG. 2 shows the qRT-PCR analysis results of transcription levels of the artificial RNA module AneR in the recombinant nitrogen-fixing engineering bacterial strains *P. stutzeri* (pAneR), *K. pneumoniae* (pAneR), and *A. vinelandii* (pAneR) under nitrogen fixation conditions.

SEQUENCE INFORMATION

Figure 3:
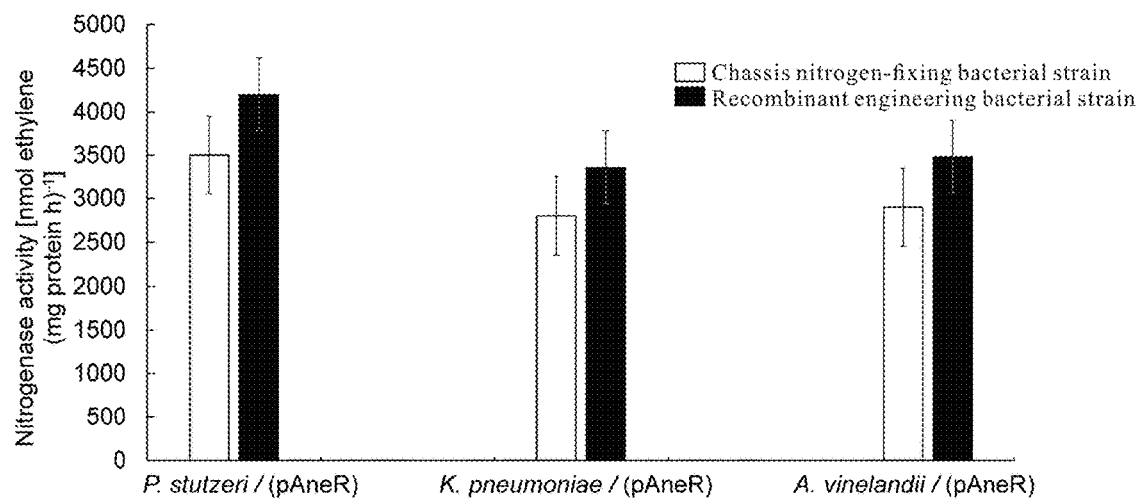
FIG. 3 shows the determination results of nitrogenase activity in each of the chassis bacterial strains and recombinant engineering bacterial strains *P. stutzeri* (pAneR), *K. pneumoniae* (pAneR), and *A. vinelandii* (pAneR).

SEQ ID NO: 1: A nucleotide sequence of the artificial RNA module AneR.

SEQ ID NO: 2: A nucleotide sequence of an artificial RNA AneR coding gene.

SEQ ID NO: 3: A nucleotide sequence of a $\sigma^{54}$-dependent artificial promoter.

DETAILED DESCRIPTION OF THE EMBODIMENTS

The present disclosure will be further described below by referring to specific examples. It should be understood that these examples are provided only to describe the method of the present disclosure, rather than to limit the scope of the present disclosure. The experimental methods which are not specified with specific conditions are generally conducted under conventional conditions well known to those skilled in the art, such as conditions disclosed in *Molecular Cloning: Experiment Guide* (Sambrook et al., New York: Cold Spring Harbor Laboratory Press, 1989) or conditions recommended by manufacturers.

Example 1 Construction of an AneR-Containing Fusion Expression Vector (I) Experimental Method An artificial RNA module AneR with a total length of 505 bp was synthesized by an artificial chemical synthesis method, and the expression of the artificial RNA module was controlled by an artificial promoter element with a size of 360 bp. The artificial RNA module AneR and the expression vector pFLAα3 each were subjected to double enzyme digestion with Bam HI and Hind III. An AneR fragment recovered after the digestion was inserted into an MCS of pFLAα3 by a T4 DNA ligase. PCR sequencing was conducted for verification to obtain the AneR-containing fusion expression vector pAneR. The expression vector was transformed into three different nitrogen-fixing microbial chassis (*P. stutzeri*, *K. pneumoniae*, and *A. vinelandii*) through three-parent binding or electroporation to obtain three recombinant nitrogen-fixing engineering bacterial strains.

(II) Experimental Results

A full-length nucleic acid sequence of the artificial RNA module AneR was synthesized by an artificial chemical synthesis method, and a fusion expression vector and recombinant engineering bacterial strains to express the artificial RNA module were successfully constructed. It was verified through PCR sequencing that the fusion expression vector was correct, and it was named pAneR. The three recombinant engineering bacterial strains carrying pAneR were *P. stutzeri* (pAneR), *K. pneumoniae* (pAneR), and *A. vinelandii* (pAneR).

(III) Experimental Conclusion

The construction of the fusion expression vector and recombinant nitrogen-fixing engineering bacterial strains to express the artificial RNA module AneR was completed.

Example 2 Expression Analysis of the Artificial RNA Module AneR in the Recombinant Engineering Bacterial Strains Under Nitrogen Fixation Conditions (I) Experimental Method 1. The recombinant bacterial strains *P. stutzeri* (pAneR), *K. pneumoniae* (pAneR), and *A. vinelandii* (pAneR) each were activated in an LB liquid medium and cultivated overnight at 30° C.
2. The next day, the resulting bacterial suspension was centrifuged at 4,000 rpm for 10 min to collect bacteria cells, and the bacteria cells were washed twice with normal saline (NS).
3. The bacteria cells were suspended with NS, and $OD_{600}$ was adjusted to about 1.0.
4. The bacteria cells were cultivated under normal conditions and nitrogen fixation conditions, and $OD_{600}$ was adjusted to about 0.5.
5. The resulting culture was cultivated under shaking at 30° C. for 0.5 h and centrifuged at 8,000 rpm for 5 min to collect bacteria cells.
6. The Promega mass RNA extraction kit Z3741 was used to extract bacterial total RNA, and the same amount of sample RNA was reverse-transcribed into single-stranded DNA (cDNA).
7. The expression level of the artificial RNA module AneR under nitrogen fixation conditions was analyzed by qRT-PCR.

(II) Experimental Results

It was found that the transcription level of aneR in each of the three recombinant bacterial strains under nitrogen fixation conditions was significantly increased by 1.5 times or more compared with that under non-nitrogen fixation conditions.

(III) Experimental Conclusion

The artificial inducible promoter element could specifically respond to a nitrogen fixation signal, thereby initiating the high expression of the artificial RNA AneR coding gene (FIG. 2).

Example 3 Determination of the Nitrogenase Activity in Each of the Recombinant Nitrogen-Fixing Engineering Bacterial Strains (I) Experimental Method The nitrogenase activity in each of the recombinant engineering bacterial strains was determined through the internationally-recognized acetylene reduction method, and the specific steps were as follows:
1. The chassis bacterial strains *P. stutzeri*, *K. pneumoniae*, and *A. vinelandii* and the recombinant bacterial strains *P. stutzeri* (pAneR), *K. pneumoniae* (pAneR), and *A. vinelandii* (pAneR) each were activated in an LB liquid medium and cultivated overnight at 30° C.
2. The next day, the resulting bacterial suspension was centrifuged at 4,000 rpm for 10 min to collect bacteria cells, and the bacteria cells were washed twice with NS.
3. The bacteria cells were suspended with NS, $OD_{600}$ was adjusted to about 1.0, and the bacteria cells were cultivated under the following conditions:

*P. stutzeri* and Recombinant Bacterial Strain *P. stutzeri* (pAneR)

(1) A bacterial suspension was transferred to a grinding triangular flask with a K medium (without N), $OD_{600}$ was adjusted to about 0.1, and the grinding triangular flask was plugged with a rubber stopper.

(2) Argon was introduced for 3 min to expel air, a microsampler was used to inject 1% oxygen and 10% acetylene into the flask, and the bacteria were cultivated at 30° C. and 200 rpm.

*A. vinelandii* and Recombinant Bacterial Strain *A. vinelandii* (pAneR)

(1) A bacterial suspension was transferred to a grinding triangular flask with a Buik's medium (without N), $OD_{600}$ was adjusted to about 0.1, and the grinding triangular flask was plugged with a rubber stopper.

(2) A microsampler was used to inject 10% acetylene into the flask, and the bacteria were cultivated at 30° C. and 200 rpm.

*K. pneumoniae* and Recombinant Bacterial Strain *K. pneumoniae* (pAneR)

(1) A bacterial suspension was transferred to a grinding triangular flask with a sucrose-containing basic medium (without N) and helium, $OD_{600}$ was adjusted to about 0.1, and the grinding triangular flask was plugged with a rubber stopper.

(2) A microsampler was used to inject 10% acetylene into the flask, and the bacteria were cultivated at 30° C. and 200 rpm.

4. Sampling was conducted after 4 h of cultivation. 0.25 mL of gas in the triangular flask was taken with a microsampler and injected into a gas chromatograph, and peak areas of ethylene and acetylene were recorded. A sample was taken and tested every hour.

5. A total protein content in a bacterial solution in the triangular flask was determined by the Coomassie brilliant blue (CBB) method.

6. The nitrogenase activity was calculated by the following formula: nitrogenase activity=ethylene peak area×(total volume of a gas phase in the triangular flask/sampling volume)/(1 nmol ethylene standard peak area×reaction time×total bacterial protein amount).

(II) Experimental Results

The nitrogenase activity in each of the three recombinant nitrogen-fixing engineering bacterial strains was significantly improved compared with that in the corresponding chassis nitrogen-fixing bacteria.

(III) Experimental Conclusion

The artificial RNA module AneR undergoing inducible expression under nitrogen fixation conditions could significantly improve the nitrogen fixation ability of the chassis bacterial strains (FIG. 3).

Example 4 Identification of the Binding Ability of the Artificial RNA AneR to the Nitrogenase Gene nifH/nifD/nifK mRNA (I) Experimental Method 1. RNA Synthesis and Labeling nifH/nifD/nifK mRNA sequences each with a length of 30 bp required in this experiment were synthesized by Shanghai GenePharma Co., Ltd. and fluorescently labeled with 5'FAM as a probe. An artificial RNA sequence with a total length of 145 bp was prepared as a ligand through in vitro transcription.

2. Mixing of a Probe with a Ligand to Allow a Reaction

A 200 nM labeling probe and a sample for increasing an unlabeled competitor concentration (from 5 nm to 150 µM) were added to each of the 16 standard-treated capillaries, and the capillaries were allowed to stand for 5 min.

3. MST Measurement and Data Analysis

The binding ability of the RNA module to nifH/nifD/nifK mRNA was analyzed by an NT.115 instrument (NanoTemper Technologies GmbH), and a dissociation constant Kd was calculated by the following formula: Kd=[A]*[L]/[AL], where [A] represents a concentration of a free fluorescent molecule, [L] represents a concentration of a free ligand, and [AL] represents a concentration of an A/L, complex.

(II) Experimental Results

Figure 4A:
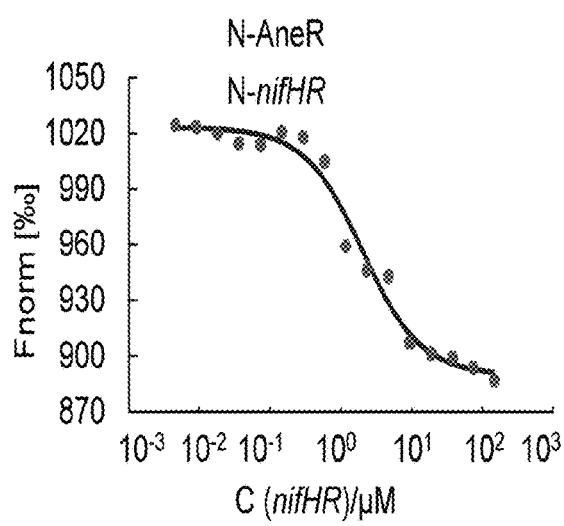
FIGS. 4A-4C show the determination results of the binding ability of the artificial RNA module AneR to the nitrogenase coding gene nifH/nifD/nifK mRNA.
Figure 4B:
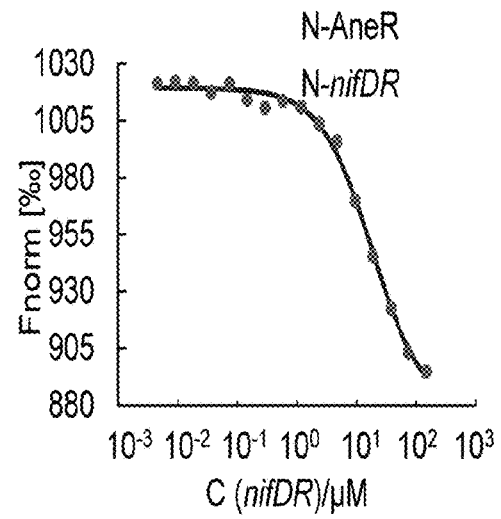
Figure 4C:
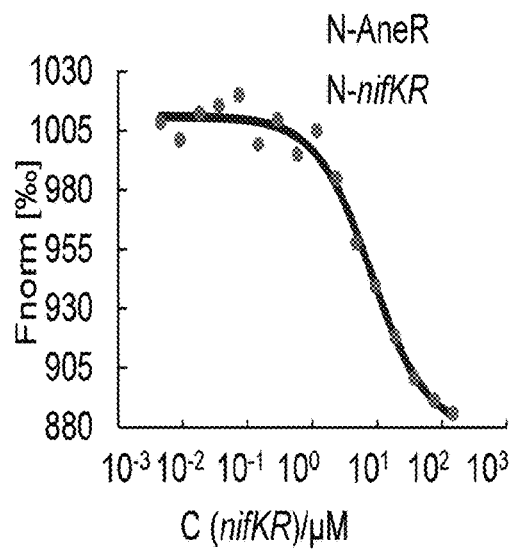

MST fitting curves of the artificial RNA AneR with nifH/nifD/nifK mRNA all are typical "S" curves, indicating that there was a prominent binding trend between the RNA AneR and nifH/nifD/nifK mRNA (FIGS. 4A-4C).

(III) Experimental Conclusion:

The artificial RNA AneR could interact with the nitrogenase gene nifH/nifD/nifK mRNA through complementary base pairing (FIGS. 4A-4C).

Example 5 Determination of the Half-Life of the Nitrogenase Gene nifHDK mRNA in Each of the Recombinant Nitrogen-Fixing Engineering Bacterial Strains (I) Experimental Method 1. The *P. stutzeri* A1501 and the recombinant bacterial strain *P. stutzeri* (pAneR) were activated in an LB liquid medium and cultivated overnight at 30° C.

2. The next day, the resulting bacterial suspension was centrifuged at 4,000 rpm for 10 min to collect bacteria cells, and the bacteria cells were washed twice with NS.

3. The bacteria cells were suspended with NS, and $OD_{600}$ was adjusted to about 1.0.

4. The bacterial suspension was transferred to a grinding triangular flask with a K medium (without N), $OD_{600}$ was adjusted to about 0.5, and the grinding triangular flask was plugged with a rubber stopper.

5. Argon was introduced for 3 min to expel air, and a microsampler was used to inject 1% oxygen and 10% acetylene into the flask.

6. The resulting culture was cultivated under shaking at 30° C. for 5 h to produce a bacterial solution.

7. A 40 mg/mL rifampicin stock solution was added to the bacterial solution, and the resulting mixture was thoroughly mixed. After the thoroughly mixed bacterial solution was treated for 0 min, 5 min, 10 min, 15 min, 20 min, 25 min, and 30 min, 2 mL of the bacterial solution was pipetted, added to a 1.5 mL EP tube, and quickly centrifuged at 12,000 rpm for 2 min, and the resulting supernatant was removed, leaving behind a bacterial precipitate.

8. 400 µL of RNAlater® (2 times a volume of rifampicin) was added to the bacterial precipitate for suspending bacteria. The resulting bacterial suspension was treated at room temperature for 5 min and quickly centrifuged, the resulting supernatant was removed, and the remaining bacterial precipitate was quickly frozen with liquid nitrogen.

9. The sample RNA was extracted and reverse-transcribed into cDNA, and the half-life of nifHDK mRNA was detected by qRT-PCR.

(II) Experimental results:

The half-life of nifH/nifD/nifK mRNA in the chassis bacterial strain *P. stutzeri* A1501 was about 20 min while the half-life of nifH/nifD/nifK mRNA in the recombinant bacterial strain *P. stutzeri* (pAneR) was about 25 min.

Figure 5:
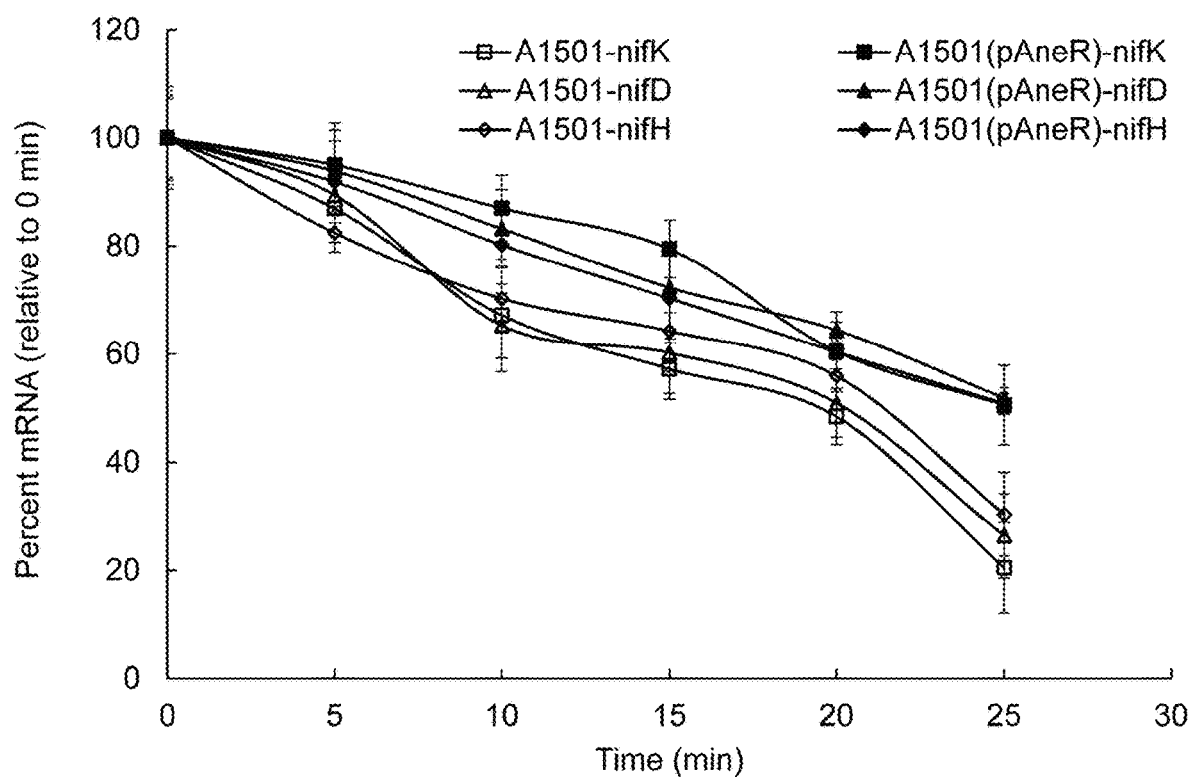
FIG. 5 shows the determination results of a half-life of the nitrogenase gene nifHDK mRNA in the chassis microorganism *P. stutzeri* A1501 and the recombinant bacterial strain *P. stutzeri* (pAneR).

(III) Experimental Conclusion:

The artificial RNA module AneR undergoing inducible expression under nitrogen fixation conditions could enhance the stability of the nitrogenase mRNA (FIG. 5).

What is claimed is:

1. An artificial RNA coding sequence with the nucleotide sequence of SEQ ID NO: 2.

2. A method of combining the artificial RNA coding sequence according to claim 1 with a nifHDK mRNA, wherein the artificial coding sequence according to claim 1 undergoes expression controlled by an artificial promoter to cause complementary base pairing with the nifHDK mRNA.

3. A method of constructing an artificial nitrogen fixation system, wherein an expression of the artificial RNA coding sequence according to claim 1 is controlled by an artificial promoter undergoing inducible expression under nitrogen fixation conditions.

4. A plasmid comprising the artificial RNA coding sequence according to claim 1.

5. A recombinant engineering bacterial strain comprising the artificial RNA coding sequence according to claim 1.

6. A method of constructing an artificial nitrogen fixation system, wherein an expression of the artificial RNA coding sequence according to claim 5 is controlled by an artificial promoter undergoing inducible expression under nitrogen fixation conditions to improve nitrogenase activity of the recombinant engineering bacterial strain.

7. An artificial RNA module comprising an artificial RNA coding sequence with the nucleotide sequence of SEQ ID NO: 2.

8. A method of constructing an artificial nitrogen fixation system, wherein an expression vector comprising the artificial RNA module according to claim 7 is fused to the artificial promoter and is constructed and transformed into three different nitrogen-fixing microbial chassis to obtain three recombinant nitrogen-fixing engineering bacterial strains.

* * * * *